United States Patent [19]

Ingwersen

[11] Patent Number: Plant 5,900

[45] Date of Patent: Mar. 10, 1987

[54] FICUS PLANT GREEN GEM

[76] Inventor: Jack D. Ingwersen, 1620 Ridgeway St., Oceanside, Calif. 92054

[21] Appl. No.: 719,005

[22] Filed: Apr. 1, 1985

[51] Int. Cl.[4] ..... A01H 5/12

[52] U.S. Cl. ..... Plt./88

[58] Field of Search ..... Plt./88

*Primary Examiner*—R. E. Bagwill

*Attorney, Agent, or Firm*—Francis X. LoJacono

[57] ABSTRACT

A *Ficus retusa nitida* Green Gem plant which is defined by an upright, compact, foliage system wherein the limbs and branches are well hidden by the full foliage which has thick leathery leaves, the upper surfaces of the leaves having a very glossy finish of an ivy-green color, and wherein the nodes are spaced in close proximity to each other along the branches and stems. The branches are bushy and bear finely shredding brown bark, and there are slender aerial roots produced near the base of the plant. The leaves are relatively elliptic and have an attenuated apex with an acute base structure, the margin thereof being revolute and undulating.

2 Drawing Figures

This invention relates to a new and distinct variety of the Ficus family of plants, and more specifically to a variety of a *Ficus retusa nitida* plant.

This new variety known as *Ficus retusa nitida* Green Gem was discovered by me as a chance mutant seedling among a group of cultivated plants in Taiwan, Republic of China. This discovery was made by me in 1982, at which time cuttings were taken from this single plant from which I hoped to develop a stock of commercial plants suitable for propagation and sale in the United States.

The present plant has been successfully asexually reproduced by me, by means of cuttings, on my property located at 1620 Ridgeway Street, Oceanside, Calif. The present variety has been asexually reproduced during the years since its discovery, and these asexual reproductions have continuously exhibited the following characteristics which clearly show that the new variety has become well established.

My new and distinct variety *Ficus retusa nitida* Green Gem is readily distinguishable from the typical *Ficus retusa nitida* in that the plant is defined by an upright, very-compact, foliage system, particularly when the plant is not pruned at its base to form a tree. Even if the plant is formed as a tree, the limbs and branches are well hidden by the full foliage—unlike those of the standard variety which has a relatively thin, open foliage system. This is well illustrated in the accompanying illustrations.

The present plant includes numerous upright or ascending branches that are of moderate caliper. Normally, no central trunk is formed as the plant naturally branches from the base. However, a trunk is well defined when pruned to form a tree, as seen in the accompanying color photographs. The older branches and trunk become relatively husky and bear finely-shreading brown bark, in contrast to the concrete gray of known varieties. Slender aerial roots are produced near the base of the plant.

The foliage is relatively heavy, causing the branches to be hidden, the stem nodes being in close proximity with each other (as illustrated in the accompanying color photographs), rather than the widely spaced nodes of the typical *Ficus retusa nitida* plant. The compact foliage system is due to the retention of the leaves on the interior portion of the branches, as opposed to that of the very-sparse, interior, foliage system of the known varieties.

A more specific characteristic of the leaves is that they will not roll up when attacked by Cuban Laurel Thrip, as with the leaves of the established varieties of the *Ficus retusa nitida.* This is in part due to their thick leathery texture and the undulating margin of the leaf.

The present new and distinct variety has been found to withstand temperatures of between 32°-100° F. without undue harm, and for shorter periods of time at as low as 29° F.

The present plant has not been observed to produce any fruit.

There are two accompanying drawings present in the form of full color photographs, one of which is employed to show the compact foliage and the individual leaf configuration with its ivy-green color. The second illustration shows the plant formed to define a self-supporting tree having a dense foliage, which is not typical to other varieties thereof. The growth pattern under coastal Southern California conditions has provided 6 to 7 feet growth within a three-year period.

In the following description of the plant, the color names and numbers used in describing the leaves are based on the nomenclature adopted by The British Horticultural Colour Charts, these being "Horticultural Chart I" and "Horticultural Chart II", issued by Wilson Colour Ltd., in collaboration with The Royal Horticultural Society. Chart I set shows "Copyright—Robert F. Wilson, 1938"; Chart II set shows "Copyright—Robert F. Wilson, 1941".

THE PLANT

Locality where grown and observed: Oceanside, Calif.

General characteristics: The plant is an upright compact shrub, branching from the base if not pruned as a tree.

Dimensions: The oldest plant pruned as a tree has reached six to seven feet in height and about three to four feet in width in a three-year period.

Branches: The plant has numerous upright or ascending branches that are of moderate caliper. Normally, no central trunk is formed as the plant naturally branches from the base. Older branches are relatively husky, bear finely shreading brown bark, and produce slender aerial roots near the base of the plant.

Foliage:

*Amount.*—Relatively heavy, hiding the branches.

*Size.*—Mature leaves are seven to nine centimeters in width. The petiole is one and one-half to two centimeters long.

*Color.*—Upper surface is approximately Ivy Green 0001060/1 and very glossy. Lower surface is approximately Spinach Green 0960/1 and dull.

*Shape.*—The leaves are elliptic with the apex attenuate-acuminate and the base acute. The margin of the leaves is entire and slightly revolute. Mature leaves are plane or more often undulate.

Venation.—The veins are fairly fine and little if any raised above the surface of the leaf. The arrangement of the veins is pinnate with the secondary veins curving near the margin and joining the superadjacent secondary vein. The lowermost pair of secondary veins arise at a more acute angle than the remaining secondary veins, and are also heavier than the others. Higher order veins arise from the outer loops of the secondary veins and branch toward the midrib.

*Arrangement.*—The arrangement of the leaves is alternate.

*Texture.*—The leaves are leathery when mature.

*Terminal stipular sheath.*—The terminal stipular sheath is conical and about two and one-half centimeters in length. The color is Fern Green 0862/1 and glossy.

Fruits: No fruits have been observed.

I claim:

1. A new and distinct variety of *Ficus retusa nitida* plant substantially as shown and described, characterized by its compact growth of foliage which has thick leathery leaves, particularly when the leaves are matured, the upper surfaces of the leaves having a very-glossy, ivy-green color, and the nodes being spaced in close proximity with each other along the branches and stems, with its older, relatively husky branches bearing finely shreading brown bark, compared to the concrete gray of *Ficus retusa nitida,* and producing slender aerial roots near the base of the plant, the configuration of the leaves being relatively elliptic with an attenuate-accuminate apex, and an acute base structure, with the margin thereof being revolute and undulating.

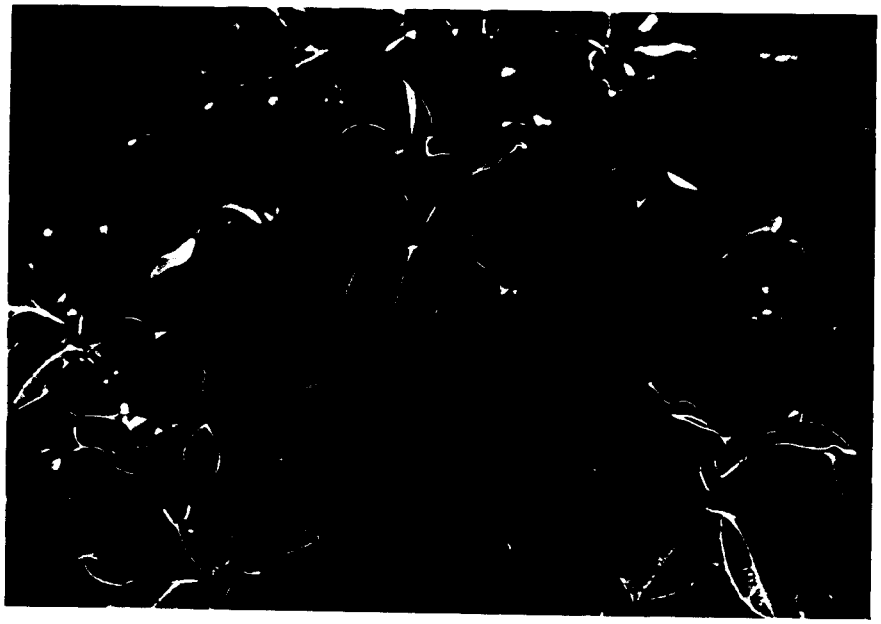
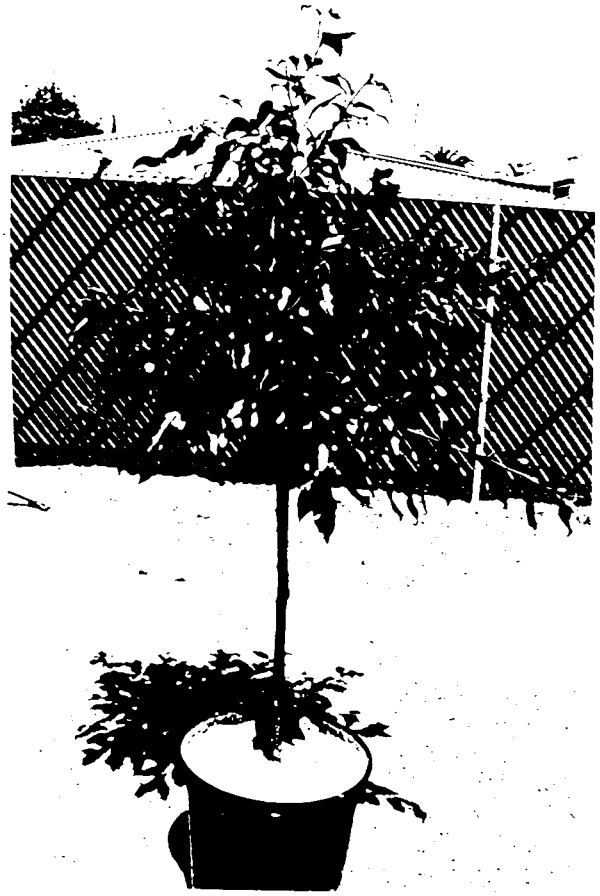

* * * * *